United States Patent [19]

Dunn

[11] Patent Number: 4,650,478
[45] Date of Patent: Mar. 17, 1987

[54] LIQUID DRAINAGE SYSTEM HAVING A HOOK SUPPORT MEMBER

[75] Inventor: William J. Dunn, Libertyville, Ill.

[73] Assignee: The Kendall Company, Boston, Mass.

[21] Appl. No.: 508,694

[22] Filed: Jun. 28, 1983

[51] Int. Cl.⁴ .............................................. A61M 1/00
[52] U.S. Cl. ..................................... 604/322; 248/95
[58] Field of Search ................... 248/95, 214, 228, 72; 211/170; 383/22, 23; 294/170; 16/110.5, 113; 604/322–326; 128/767, DIG. 24

[56] References Cited

U.S. PATENT DOCUMENTS

| | | | |
|---|---|---|---|
| 4,189,789 | 2/1980 | Hofstetter | 294/170 |
| 4,312,352 | 1/1982 | Meisch | 604/322 |
| 4,317,550 | 3/1982 | Hannah | 248/95 |
| 4,562,984 | 1/1986 | Sherlock et al. | 248/95 |

*Primary Examiner*—C. Fred Rosenbaum
*Assistant Examiner*—J. L. Kruter
*Attorney, Agent, or Firm*—Powell L. Sprunger

[57] ABSTRACT

A liquid drainage system comprising, a receptacle having a chamber to receive the liquid, and a support member adjacent an upper portion of the receptacle. The system has a support hook having an outwardly directed first bar, and a downwardly directed second bar extending from an outer portion of the first bar. The system has a device for pivotally connecting the hook to the support member such that the hook is movable between a first position generally perpendicular to the support member and a second position generally aligned with the support member.

2 Claims, 7 Drawing Figures

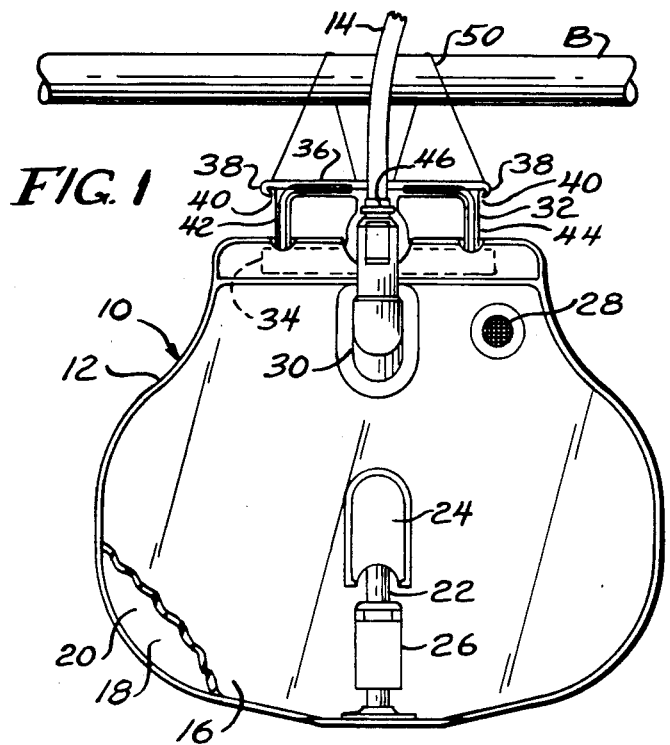
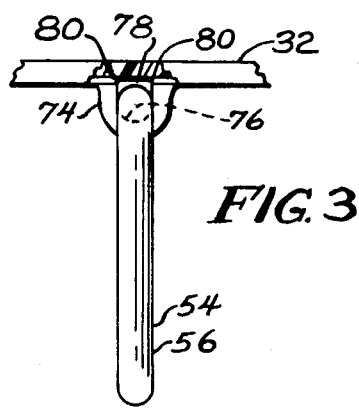
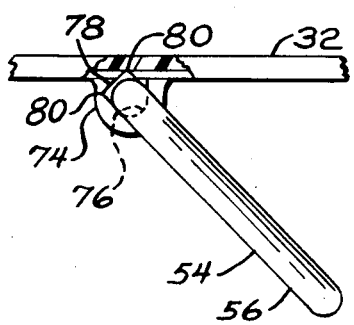
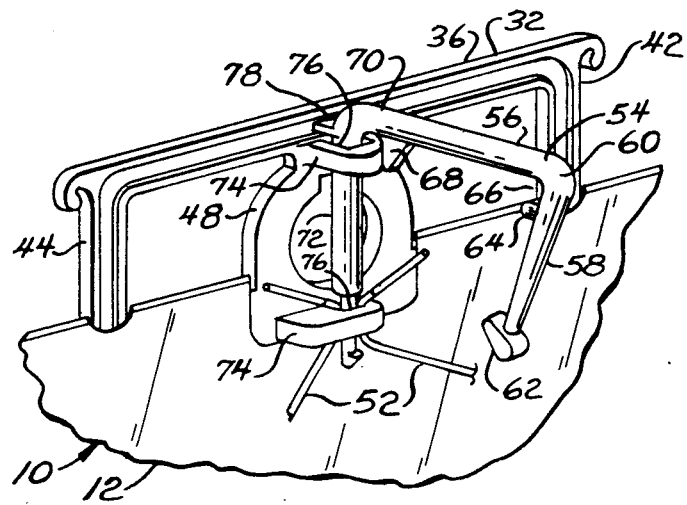
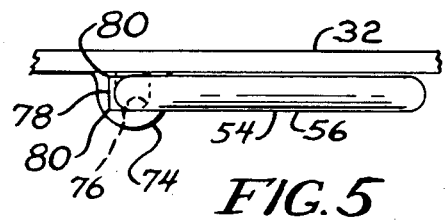
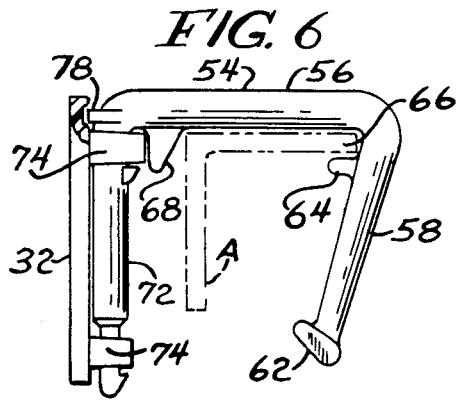
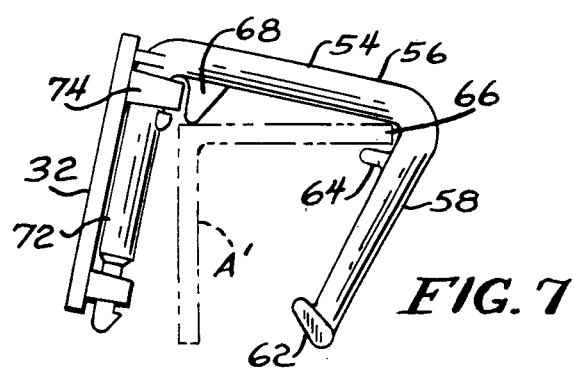

LIQUID DRAINAGE SYSTEM HAVING A HOOK SUPPORT MEMBER

BACKGROUND OF THE INVENTION

The present invention relates to liquid drainage systems.

In the past, urine drainage systems have been known. Such systems may comprise a catheter which is passed through the urethra of a patient until a distal end of the catheter is located in the bladder, a drainage tube connected to a proximal end of the catheter outside the patient's body, and a collection bag connected to a downstream end of the drainage tube. In use, urine drains from the bladder through the catheter and drainage tube into the bag for collection therein.

Although such systems have operated satisfactorily, it has been found difficult and tedius to connect the bag to a support object, such as a bed rail, and it is thus desirable to improve the manner in which the bag is supported.

SUMMARY OF THE INVENTION

A principal feature of the present invention is the provision of an improved liquid drainage system.

The system of the present invention comprises a receptacle having a chamber to receive the liquid, and a support member adjacent an upper portion of the receptacle. The system has a support hook having an outwardly directed first bar, and a downwardly directed second bar extending from an outer portion of the first bar. The system also has means for pivotally connecting the hook to the support member.

A feature of the present invention is that the hook is movable between a first position generally perpendicular to the support member and a second position generally aligned with the support member.

Another feature of the invention is that the hook may be placed over a support object when the hook is at the first position.

Yet another feature of the invention is that the hook may be moved to the second position in order to carry the receptacle.

A further feature of the invention is the provision of means for maintaining the hook in the first position.

Still another feature of the invention is that the second bar may have an upwardly and inwardly directed boss adjacent an outer end thereof to hook underneath a cylindrical rail.

A further feature of the invention is that the second bar may have an inwardly directed boss slightly spaced from the first bar to define a slot between the boss and first bar to receive an angle iron.

Yet another feature of the invention is that the first bar may include a downwardly directed tapered boss extending from an inner portion of the first bar in order to direct the angle iron toward the slot.

Still another feature of the invention is that the support member may have a pair of opposed spaced ears defining slots, and the receptacle may have a cord loop secured to an upper portion of the receptacle, such that the loop may be received over a support bar and in the ears, with the loop extending between the ears.

Further features will become more fully apparent in the following description of the embodiments of this invention and from the appended claims.

DESCRIPTION OF THE DRAWINGS

In the drawings:

FIG. 1 is a fragmentary plan view of a liquid drainage system of the present invention illustrating a cord loop which is passed over a support bar in order to support a receptacle of the system;

FIG. 2 is a rear fragmentary perspective view of the system illustrating a hook in a position generally perpendicular to a support bar;

FIG. 3 is a fragmentary upper plan view of the system of FIG. 2;

FIG. 4 is a fragmentary upper plan view illustrating the hook as moved partially toward the support bar;

FIG. 5 is a fragmentary upper plan view illustrating the hook as moved to a position generally aligned with the support bar;

FIG. 6 is a fragmentary side view illustrating the hook as supported on a smaller angle iron; and FIG. 7 is a fragmentary side view illustrating the hook as being supported on a larger angle iron.

DESCRIPTION OF THE PREFERRED EMBODIMENTS

Referring now to FIG. 1, there is shown a liquid drainage system generally designated 10 having a receptacle 12 and a drainage tube 14. The receptacle 12 has a front wall 16 of flexible plastic material, and a back wall 18 of flexible plastic material, with the front and back walls 16 and 18 being joined at their periphery in order to define a chamber 20 therebetween. The receptacle 12 may have a tubular section 22 connected to a lower portion of the front wall 16 and communicating with the chamber 20, with the tubular section 22 being received in a pocket 24 in a storage position of the tubular section 22. When it is desired to drain urine from the receptacle 12, the tubular section 22 is removed from the pocket 24, and a clamp 26 of known type is opened to permit passage of urine through the tubular section 22 until the chamber 20 is emptied. After drainage of urine from the receptacle 12, the clamp 26 is again closed, and the tubular section 22 is inserted into the pocket 24. The receptacle 12 preferably has a vent 28 having a bacteria filter of known type to filter bacteria from the air passing from the atmosphere into the chamber 20. The receptacle 12 has a connector 30 connected to an upper portion of the front wall 16, such that the connector 30 communicates with the chamber 20. As shown, a downstream end of the drainage tube 14 is connected to the connector 30, such that the drainage tube 14 also communicates with the chamber 20.

In use, a catheter (not shown) is passed through the urethra of a patient until a distal end of the catheter is located in the patient's bladder. During catheterization, urine drains from the bladder through the catheter and drainage tube 14 into the receptacle chamber 20 for collection therein.

With reference to FIGS. 1 and 2, the receptacle 12 has a support member 32 which may be constructed from a suitable plastic material. The support member 32 has an elongated lower bar 34 which is secured between the front wall 16 and the back wall 18 in order to anchor the support member 32 in place. The support member 32 also has an elongated upper bar 36 having a pair of opposed spaced ears 38 at the outer end thereof defining a pair of slots 40. The support member 32 also has a pair of upright posts 42 and 44 connecting the lower bar 34 and upper bar 36. The support member 32 has an outwardly directed ring 46 extending from a central portion 48 of the support member 32, with the ring 46 being received on an upper portion of the connector 30 in order to retain the connector 30 in place.

With further reference to FIGS. 1 and 2, the receptacle 12 has a cord loop 50 having inner ends 52 secured to a back portion of the support member 32. The cord loop 50 may be passed over a support bar B, and the cord loop 50 may be received in the slots 40 of the ears 38, with the loop 50 extending between the ears 38 along the support member 32, such that the receptacle 12 may readily be supported by the cord loop 50 over the bar B.

With reference to FIG. 2, the receptacle 12 has a support hook 54 which may be constructed from a suitable flexible plastic material, with the hook 54 being connected to the support member 32. The hook 54 has an outwardly directed first bar 56, and a generally downwardly directed second bar 58 extending at an acute angle from an outer portion 60 of the first bar 56 toward the receptacle 12. The second bar 58 has an upwardly and inwardly directed boss 62 adjacent an outer end thereof. When the hook 54 is located at a position generally perpendicular to the support member 32, as shown in FIG. 2, the hook 54 may be placed over a cylindrical bed rail of standard dimensions, with the second bar 58 flexing about the rail until the hook 54 snaps in place with the boss 62 located beneath the rail. In this manner, the hook 54 may be placed over the cylindrical rail in order to support the receptacle 12 from the rail.

The second bar 58 has an inwardly directed boss 64 slightly spaced from the first bar 56 in order to define a slot 66 between the boss 64 and the first bar 56. The hook 54 also has a downwardly directed tapered boss 68 extending from an inner portion 70 of the first bar 56. With reference to FIG. 6, when the hook 54 is located generally perpendicular to the support member 32, the hook 54 may be placed over an angle iron A of smaller standard dimensions, with the boss 68 guiding the angle iron A into the slot 66, in order for the angle iron A to support the receptacle 12 by the hook 54. In an alternative manner, with reference to FIG. 7, the hook 54 may be supported on an angle iron A' of larger standard dimensions, with the angle iron A' resting on a lower portion of the boss 68 and being received in the slot 66. In this manner, the receptacle 12 may be supported by the hook 54 on the angle iron A'.

With reference to FIG. 2, the hook 54 has a downwardly directed third bar 72 extending from the inner portion 70 of the first bar 56. The support member 32 has a pair of vertically spaced pivot members 74 having openings 76 extending therethrough which pivotally receive the third bar 72, such that the hook 54 may be moved between the first position generally perpendicular to the support member 32 and a pair of opposed second positions generally aligned with the support member 32. With reference to FIGS. 2 and 3, the hook 54 has a generally flat flange 78 extending inwardly from the hook 54 and being closely spaced from the support member 32 when the hook 54 is in the first position. As shown, the flange 78 has a pair of opposed and aligned spaced corners 80 which engage against the support member 32 if the hook 54 is turned slightly from the perpendicular first position in order to maintain the hook 54 in the first position, as shown in FIGS. 2 and 3. However, with reference to FIG. 4, if the hook 54 is turned with some force, the hook 54 and support member 32 flex in order to permit passage of the corners 80 past the support member 32, such that the hook 54 may be moved to the second position, as shown in FIG. 5, generally aligned with the support member 32. Of course, the hook 54 may be moved in the opposite direction, such that the hook 54 is aligned with the other side of the support member 32. Thus, in this manner, the hook 54 may be maintained in its first support position in order to hook the receptacle 12 onto a bed rail or other suitable object, or the hook 54 may be moved to the second position aligned with the support member 32 to permit convenient carrying of the receptacle 12 without obstruction by the hook 54.

The foregoing detailed description is given for clearness of understanding only, and no unnecessary limitations should be understood therefrom, as modifications will be obvious to those skilled in the art.

I claim:

1. A liquid drainage system, comprising:
   a receptacle having a chamber to receive the liquid;
   a support member adjacent an upper portion of the receptacle; and
   a support hook connected to the support member, said hook having an outwardly directed first bar, said first bar having an inner and outer portion, and a downwardly directed second bar extending from said outer portion of the first bar, said second bar having an inwardly directed boss slightly spaced from the first bar to define a slot between the boss and first bar, including a downwardly directed tapered boss extending from said inner portion of the first bar.

2. A liquid drainage system, comprising:
   a receptacle having a chamber to receive the liquid;
   a support member adjacent an upper portion of the receptacle;
   a support hook having an outwardly directed first bar, and a downwardly directed second bar extending from an outer portion of the first bar; and
   means for pivotally connecting the hook to the support member such that the hook is movable between a first position generally perpendicular to the support member and a second position generally aligned with the support member, including means for maintaining said hook in said first position cooperating between the support member and hook the maintaining means comprising a flange extending inwardly from the hook and being closely spaced from the support member when said hook is in the first position, said flange having a pair of opposed and aligned spaced corners.

* * * * *